United States Patent [19]

Fernholz et al.

[11] Patent Number: 4,668,819

[45] Date of Patent: May 26, 1987

[54] PROCESS FOR THE MANUFACTURE OF UNSATURATED ESTERS OF CARBOXYLIC ACIDS

[75] Inventors: Hans Fernholz, Fischbach; Hans Krekeler, Wiesbaden; Günter Roscher, Kelkheim; Hans-Joachim Schmidt, Falkenstein; Heinz Schmitz, Frankfurt am Main; Friedrich Wunder, Flörsheim, all of Fed. Rep. of Germany

[73] Assignee: Hoechst Aktiengesellschaft, Frankfurt, Fed. Rep. of Germany

[21] Appl. No.: 755,080

[22] Filed: Jul. 15, 1985

Related U.S. Application Data

[63] Continuation of Ser. No. 420,097, Sep. 20, 1982, abandoned, which is a continuation of Ser. No. 922,377, Jul. 6, 1978, abandoned, which is a continuation of Ser. No. 602,895, Aug. 7, 1975, abandoned, which is a continuation of Ser. No. 454,779, Mar. 25, 1974, abandoned.

[30] Foreign Application Priority Data

Mar. 26, 1973 [DE] Fed. Rep. of Germany ....... 2315037

[51] Int. Cl.$^4$ ............................................. C07C 67/055
[52] U.S. Cl. ...................................................... 560/245
[58] Field of Search .......................................... 560/245

[56] References Cited

U.S. PATENT DOCUMENTS

| | | | |
|---|---|---|---|
| 3,546,278 | 12/1970 | Haydon | 260/497 |
| 3,567,767 | 3/1971 | Yasui | 560/245 |
| 3,625,998 | 12/1971 | Fernholz | 560/245 |
| 3,634,496 | 1/1972 | Kominami | 560/245 |
| 3,658,888 | 4/1972 | Hornig | 260/497 |
| 3,670,014 | 6/1972 | Fernholz | 560/245 |
| 3,759,839 | 9/1973 | Fernholz | 252/431 |
| 3,761,513 | 9/1973 | Sennewald | 560/245 |
| 3,847,972 | 11/1974 | Kominami | 560/245 |
| 3,917,676 | 11/1975 | Kasaki | 560/245 |
| 3,939,199 | 2/1976 | Fernholz | 560/245 |
| 3,950,400 | 4/1976 | Fernholz | 560/245 |

FOREIGN PATENT DOCUMENTS

| | | |
|---|---|---|
| 781491 | 3/1968 | Canada . |
| 851745 | 9/1970 | Canada . |
| 902103 | 6/1972 | Canada . |
| 2100778 | 7/1972 | Fed. Rep. of Germany . |
| 46-4362 | 2/1971 | Japan . |
| 46-13723 | 4/1971 | Japan . |
| 46-23365 | 7/1971 | Japan . |
| 1017938 | 1/1966 | United Kingdom . |
| 1063434 | 3/1967 | United Kingdom . |
| 1082845 | 9/1967 | United Kingdom . |
| 1128993 | 10/1968 | United Kingdom . |
| 1203953 | 9/1970 | United Kingdom . |
| 1209125 | 10/1970 | United Kingdom . |
| 1211096 | 11/1970 | United Kingdom . |
| 1269742 | 4/1972 | United Kingdom . |

OTHER PUBLICATIONS

Moisejev et al Doklady Akademii Nauk, vol. 133, No. 2, pp. 377–380 (1960).

*Primary Examiner*—Michael L. Shippen
*Attorney, Agent, or Firm*—Curtis, Morris & Safford

[57] ABSTRACT

Unsaturated esters of carboxylic acids are prepared by reacting olefines or cycloolefines with carboxylic acids and oxygen in the gaseous phase in the presence of a catalyst containing noble metal salts or noble metals of the VIII$^{th}$ group of the Periodic System and alcali metal salts and/or alcaline earth metal salts, as activators the content of noble metal being in the range of from 1.2 to 5% by weight and the proportion of the metal fraction of each individual activator to the noble metal content being in the range of from 0.5 to 1 to 3:1.

4 Claims, No Drawings

PROCESS FOR THE MANUFACTURE OF UNSATURATED ESTERS OF CARBOXYLIC ACIDS

This application is a continuation of application Ser. No. 420,097, filed Sept. 20, 1982, abandoned, which is a continuation of Ser. No. 922,377, filed July 6, 1978, now abandoned, which is a continuation of Ser. No. 602,895, filed Aug. 7, 1985, now abandoned, which is a continuation of Ser. No. 454,779, filed Mar. 25, 1974, now abandoned.

The manufacture of unsaturated esters of carboxylic acids by reacting olefines with oxygen and carboxylic acids in the presence of catalysts containing noble metals or their salts or mixtures thereof is well known. The process is performed mostly in the gaseous phase at normal pressures or at pressures of up to 25 atm. and at temperatures ranging from 100° to 250° C.

The catalysts used consist of noble metal salts or noble metals themselves of the VIII$^{th}$ and optionally in addition the I$^{st}$ sub-group of the Periodic System—particularly palladium and is salts and optionally in addition gold—or the mixtures thereof on carrier materials which may contain as activators—for example—alcali metal salts, alcaline earth metal salts, cadmium salts, gold salts or bismuth salts. Carrier materials are, for example, silicic acid, aluminium oxide, spinels, pumice, active carbon. The catalysts are generally used in spherical shape, as extruded pieces, tablets, or irregular granules.

The space/time yield of ester (quantity of ester formed per hour) is of fundamental importance to the rentability of the process.

Therefore, the literature includes numerous descriptions of steps to be taken for increasing the space/time yield of ester by modification of the reaction conditions or of the catalyst system. The space/time yield of ester may thus be improved, for example, by increasing the reaction temperature and the reaction pressure. However, these possibilities are limited, because any catalyst presents the inconvenience that above a certain temperature limit the formation of carbon dioxide as a by-product increases considerably at the cost of the formation of ester. Generally, the most fabourable temperature range stretches from 150° to 200° C. Furthermore, the formation of ester is also influenced favourably by increasing the reaction pressure.

The space/time yield of ester also depends on the concentration of oxygen in the reaction mixture. The limit of inflammability of the reaction mixture shifting to lower oxygen concentration with the pressure increasing, the possibility to ameliorate the output by increasing the pressure is but limited, too. Therefore, it is usual practice in the art to use reaction pressures from 5 to 10 atmospheres. Further possibilities to enhance the space/time yields of ester may be seen in a modification of the carrier materials used for the catalytically active components or of the particle size of the carrier materials as well. These factors helped, for example, to realize space/time outputs of up to 495 g/l per hour for vinyl acetate in fixed bed reactors.

It has now been found, surprisingly, that the space/time output of known catalysts may be considerably increased, by raising within a narrow range the content of noble metal and of activators, whereas the proportion of noble metal content to activator content is modified. In case that the noble metal content only is raised, no distinctly positive effect is obtained, neither does an aliquot increase of the activator quantity, corresponding to the increase of th noble metal proportion, bring about a noticeable increase of the space/time yield of ester. The contents in noble metal of the catalyst exceeding a certain limit, the space/time output does not improve considerably. These statements are proved by comparing the results of the following examples. When comparing example Ia) to Ih), it can be seen that e.g. in the case of vinyl acetate, based on a known standard contact (Example Ia), increasing the noble metal content from 1 to 5 wt.% yields an increase of the vinyl acetate space/time yield from 320 g/l per hour to 360 g/l per hour only. When further comparing Examples Ia to Ib and Ic, it is evidenced that an aliquot increase of the noble metal content and of the activator content in respect to the standard contact of Example Ia is only able to raise the vinyl acetate space/time yield by 20 or 40 g/l per hour. On the other hand and contrary to the aforesaid it has been found, surprisingly, that increasing the quantity of noble metals and activators in a determined proportion such as shown in Examples Id and Ig results in a vinyl acetate space/time yield of up to 903 g/l per hour.

The process according to the present invention is particularly well suitable for preparing vinyl acetate from acetic acid and ethylene, but it is also applicable for preparing further unsaturated esters when using olefines other than ethylene, such as propylene, isobutylene, butylene, pentene, hexene or cycloolefines, such as cyclohexene, provided that the known catalysts used for the individual olefine or cycloolefine be modified according to the present invention. In case that allyl acetate is made of propylene, acetic acid and oxygen, by the a.m. method the space/time output is raised from originally 370 g/l per hour to 750 g/l per hour.

The present invention provides a method for the preparation of unsaturated esters of carboxylic acids by the reaction of olefines or cycloolefines with carboxylic acids and oxygen in the gaseous phase, in the presence of catalysts containing noble metal salts or noble metals of the VIII$^{th}$ subgroup of the Periodic System as well as alcali metal salts and/or alcaline earth metal salts as activators, optionally in admixture with other salts, on carrier materials, at temperatures of from 100° to 250° C. and pressures of from 2 to 20 atmospheres, wherein the noble metal net content of the catalyst is in the range of from 1.2 to 5 wt.% and the proportion of the metal fraction of each individual activator to the nobel metal content is from 0.5:1 to 3:1, preferably the noble metal content being from 1.3 to 3 wt.% and the proportion of the metal fraction of each individual activator to the noble metal content being preferably from 0.7:1 to 2:1, particularly from 1:1 to 2:1.

The process according to the present invention not only allows for considerably increasing the space/time yield of ester compared to that of the former processes, but the conversion rates of the carboxylic acid used and the olefine used increase, too. This leads to a higher concentration of ester in the condensation products to be processed. Processing more concentrated ester solutions requires lower costs and efforts for their distillation than the separation of diluted mixtures by distillation.

The following examples illustrate the invention; reference being made to the accompanying flow scheme.

Mode of operation:

The mixture of olefin or cycloolefine, oxygen and $CO_2$ is directed through a carboxylic acid evaporator (1) constructed as a bubble column, where the gas current is charged with the corresponding carboxylic acid. The gaseous mixture, upon leaving the carboxylic acid evaporator (1), travels to the reactor (2) through a mantled, steam-heated pipe. The reactor is a jacketed tube having a length of 5.60 m and an internal diameter of 32 mm containing 4.4 liters of catalyst. The reaction heat is eliminated by means of water in the outer jacket.

The gaseous mixture is cooled to abt. 5° C. in the brine cooled condenser (3) upon leaving the reactor. The condensable fractions—non-reacted carboxylic acid, formed ester, water—are liquefied, sent through the intermediate container (4) and released in the collector (5). The remaining residual gas composed of non-reacted oxygen, non-reacted olefine or cycloolefine, $CO_2$ formed as by-product—is fed back into the reaction through the compressor (6).

Through the pressure valve at the suction-side of the compressor the spent olefine is replaced by fresh olefine. Oxygen is replenished at the pressure-side of the compressor. For maintaining steady operating conditions, $CO_2$ formed during the reaction as a by-product, is eliminated from the system as waste gas.

EXAMPLES

I. Preparation of vinyl acetate (a) 4.4 ltrs. of silicic acid carrier in spherical shape, having a diameter of from 4–6 mm, are impregnated with an acetic acid solution composed of palladium acetate, potassium acetate, cadmium acetate. After drying, the catalyst contains 1 wt.% of palladium, 1.5 wt.% of cadmium and 1.9 wt.% of potassium, present as acetates.

A gaseous mixture consisting of

| ethylene | 58.6 vol. % |
| acetic acid (calc. mol. wt. 60) | 15 vol. % |
| oxygen | 6.4 vol. % |
| $CO_2$, inert materials | 20 vol. % | is passed over the catalyst at the rate of 20 $Nm^3$ per hour.

The temperature inside the catalyst is adjusted to 183° C. by means of a corresponding regulation of the steam pressure in the outer jacket of the reactor.

The pressure at the reactor inlet is adjusted to 9 atmospheres.

8.7 kg per hour of a mixture composed as follows

| acetic acid | 80.5 wt. % |
| vinyl acetate | 16.1 wt. % |
| water | 3.4 wt. % | are obtained in the condensate container (5).

The space-time yield of vinyl acetate amounts to 320 g/l per hour.

(b) Procedure and reaction conditions are the same as described for Example Ia. The reactor contains 4.4 liters of a catalyst with the same carrier material as specified according to (a), the catalyst contains however, 1.5 wt.% of palladium, 2.25 wt.% of cadmium, 2.9 wt.% of potassium, present as acetates.

Crude condensate is obtained at the rate of 8.85 kg per hour.

The composition is as follows:

| acetic acid | 79.0 wt. % |
| vinyl acetate | 17.0 wt. % |
| water | 4.0 wt. % |

The space/time yield of vinyl acetate amounts to 340 g/l per hour.

(c) Procedure and reaction conditions are the same as described for Example Ia. However, the catalyst contains 2.5 wt.% of palladium, 3.7 wt.% of cadmium, 4.7 wt.% of potassium, present as acetates.

Crude condensate is obtained at the rate of 8.9 kg per hour, having the following composition

| acetic acid | 77.2 wt. % |
| vinyl acetate | 17.8 wt. % |
| water | 5.0 wt. % |

The space/time yield of vinyl acetate amounts to 360 g/l per hour.

(d) Procedure and reaction conditions are the same as described for Example Ia. However, the catalyst contains 2.0 wt.% of palladium, 1.8 wt.% of cadmium, 2.0 wt.% of potassium, present as acetates.

Crude condensate is obtained at the rate of 10.0 kg per hour, having the following composition:

| acetic acid | 53.1 wt. % |
| vinyl acetate | 37.6 wt. % |
| water | 9.3 wt. % |

The space/time yield of vinyl acetate amounts to 835 g/l per hour.

(g) Procedure and reaction conditions are the same as described for Example Ia.

The catalyst contains 2.5 wt.% of palladium, 1.8 wt.% of cadmium, 2.0 wt.% of potassium, present as acetates.

Crude condensate is obtained at the rate of 10.2 kg per hour, having the following composition:

| acetic acid | 51.3 wt. % |
| vinyl acetate | 39.0 wt. % |
| water | 9.7 wt. % |

The space/time yield of vinyl acetate amounts to 903 g/l per hour.

(h) Procedure and reaction conditions are the same as described for Example Ia.

The catalyst contains 5 wt.% of palladium, 1.8 wt.% of cadmium, 2 wt.% of potassium, present as acetates.

Crude condensate is obtained at the rate of 8.9 kg per hour, having the following composition:

| acetic acid | 77.0 wt. % |
| vinyl acetate | 17.7 wt. % |
| water | 5.3 wt. % |

The space/time yield of vinyl acetate amounts to 360 g/l per hour.

(i) Procedure and reaction conditions are the same as described for Example Ia.

According to Example Ia, 4.4 liters of the carrier material are impregnated with an acetic acid solution of palladium acetate, potassium acetate, barium aurate.

After drying, the catalyst contains 1.4 wt.% of palladium, 0.4 wt.% of gold, 2.0 wt.% of potassium and 0.3 wt.% of barium.

Crude condensate is obtained at the rate of 9.7 kg per hour, having the following composition:

|             |          |
|-------------|----------|
| acetic acid | 58.7 wt. % |
| vinyl acetate | 33.9 wt. % |
| water | 7.4 wt. % |

The space/time yield of vinyl acetate amounts to 746 g/l per hour.

II. Allyl acetate

The apparatus is identical to that of Examples Ia-i. The reaction temperature is 185° C., the pressure at the reactor inlet is 7.0 atm.

At the rate of 11.4 Nm$^3$ per hour, a gas of the following composition passes the reactor:

|             |          |
|-------------|----------|
| propylene | 40 vol % |
| acetic acid (calc. mol. wt. 60) | 20.8 vol. % |
| CO$_2$ and inert materials | 31.7 vol. % |
| oxygen | 7.5 vol. % |

(a) 4.4 liters of the carrier material according to Example Ia are impregnated with an acetic acid solution of palladium acetate, barium aurate, bismuth acetate, potassium acetate. After drying, the catalyst contains 0.9 wt.% of palladium, 0.3 wt.% gold, 1.2 wt.% of bismuth, 2.9 wt.% of potassium.

Under the specified reaction conditions 7.3 kg per hour of crude condensate are obtained having the following composition:

|             |          |
|-------------|----------|
| acetic acid | 72.6 wt. % |
| allyl acetate | 22.2 wt. % |
| water | 5.2 wt. % |

The space/time yield of allyl acetate is 370 g/l per hour.

(b) Procedure and reaction conditions are the same as described for Example IIa.

After drying, the catalyst contains 1.8 wt.% of palladium, 0.5 wt.% of gold, 1.22 wt.% of bismuth, 2.9 wt.% of potassium.

Crude condensate is obtained at the rate of 8.5 kg per hour, having the following composition:

|             |          |
|-------------|----------|
| acetic acid | 50.7 wt. % |
| allyl acetate | 40.0 wt. % |
| water | 9.3 wt. % |

The space/time yield of allyl acetate is 750 g/l per hour.

(c) Procedure and reaction conditions are the same as described for Examples IIa and b.

The catalyst contains 1.8 wt.% of palladium, 0.5 wt.% of gold, 2.4 wt.wt.% of bismuth, 5.8 wt.% of potassium.

Crude condensate is obtained at the rate of 7.4 kg per hour, having the following composition:

|             |          |
|-------------|----------|
| acetic acid | 71.2 wt. % |
| allyl acetate | 22.7 wt. % |
| water | 6.1 wt. % |

The space/time yield of allyl acetate amounts to 380 g/l per hour.

What is claimed is:

1. A process for the preparation of vinyl acetate comprising reacting ethylene with acetic acid and oxygen in a gaseous phase in the presence of a catalyst supported on silicic acid as a carrier and containing as a noble metal component palladium or a palladium salt, and containing as an activator potassium and cadmium, at a temperature of 100° to 250° C. at a pressure from 2 to 20 atmospheres, wherein the content of palladium in the catalyst is 1.3 to 3 weight percent calculated on an elemental basis and wherein the proportion by elemental weight of potassium to palladium is from 0.8:1 to 1.0:1 and the proportion by elemental weight of cadmium to palladium is from 0.7:1 to 2:1.

2. The process, as claimed in claim 1, wherein the content of palladium is 2 to 2.5 weight percent, the proportion of potassium to palladium is from 0.8:1 to 1.0:1 and the proportion of cadmium to palladium is from 0.72:1 to 0.9:1.

3. The process, as claimed in claim 1, wherein the content of palladium is about 2.5 weight percent, the proportion of potassium to palladium is about 0.8:1 and the proportion of cadmium to palladium is about 0.72:1.

4. The process, as claimed in claim 1 wherein the content of palladium is about 2.0 weight percent, the proportion of potassium to palladium is about 1.0:1 and the proportion of cadmium to palladium is about 0.9:1.

* * * * *